US00PP34768P2

(12) United States Plant Patent
NeSmith

(10) Patent No.: US PP34,768 P2
(45) Date of Patent: Nov. 29, 2022

(54) SOUTHERN HIGHBUSH BLUEBERRY PLANT NAMED 'TH-896'

(50) Latin Name: *Vaccinium corymbosum*
Varietal Denomination: 'TH-896'

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/575,314

(22) Filed: Jan. 13, 2022

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ... A01H 5/08; A01H 5/00; A01H 5/02; A01H 6/36; A01H 6/368
See application file for complete search history.

*Primary Examiner* — June Hwu
(74) *Attorney, Agent, or Firm* — Thomas Horstemeyer, LLP

(57) ABSTRACT

A new and distinct cultivar of *Vaccinium* plant named 'TH-896', characterized by a combination of early to mid-season ripening and flowering; large berries with good flavor, firmness, and scar; and a medium chilling requirement of about 300-400 hours, or more, below about 45° F.

6 Drawing Sheets

Botanical designation: *Vaccinium corymbosum.*
Cultivar denomination 'TH-896'.

BACKGROUND OF THE INVENTION

The present invention relates to a new and distinct cultivar of southern highbush blueberry plant, botanically know as *Vaccinium corymbosum*, and hereinafter referred to by the cultivar name 'TH-896'.

The new *Vaccinium corymbosum* 'TH-896' was first identified in 2005 in Griffin, Ga. The new variety 'TH-896' is early to mid-season for flowering time and ripening. 'TH-896' has large berries with good scar, color, firmness and flavor as compared to other representative cultivars. It is estimated to have a chilling requirement of about 300 to 400 hours, or more, below 45° F. when produced under typical low to mid chill production areas in temperate regions. 'TH-896' is able to produce high-quality fruit when grown in conventional production areas.

'TH-896' is a product of a cross of *Vaccinium corymbosum* 'TH-622' (non-patented breeding selection) X 'Bluecrisp' (U.S. Plant Pat. No. 11,033) made in 2002 by D. Scott NeSmith. The new blueberry plant variety 'TH-896' has been tested in asexually propagated (by softwood vegetative cuttings from current year's growth) plantings in Alapaha, Ga. since 2007 where it was established for testing and comparing to industry standards. Observations of the resulting 'TH-896' progeny have shown that the unique features of this new *Vaccinium corymbosum* 'TH-896' are stable and reproduced true to type in successive generations.

SUMMARY OF THE INVENTION

The new *Vaccinium* cultivar 'TH-896' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium corymbosum* cultivar named 'TH-896'. In combination, these traits set 'TH-896' apart from all other existing varieties of southern highbush blueberry known to the inventor:

1. Early to mid-season, flowering before 'TH-622' and later than 'Bluecrisp' (U.S. Plant Pat. No. 11,033);
2. ripening before 'TH-622' and later than the early variety 'Suziblue' (U.S. Plant Pat. No. 21,167), but similar to the time of 'Camellia' (U.S. Plant Pat. No. 18,151) in South Georgia;
3. as compared to 'Suziblue' and 'Camellia', produces berries that have flavor with more well-balanced acidity to sweetness, have smaller scar, and are firmer; and
4. medium chilling requirement of about 300-400 hours, or more, below about 45° F. (based on comparison of flowering dates with those of known standard cultivars) when produced under typical low to mid chill production areas in temperate regions;

As compared to the female parent 'TH-622', plants of *Vaccinium* 'TH-896' have a lower chilling requirement, earlier flowering and ripening times, and are firmer.

As compared to the male parent 'Bluecrisp', plants of *Vaccinium* 'TH-896' have a similar chilling requirement, later flowering and ripening times, are larger, and have lighter blue color.

Plants of the new *Vaccinium* can also be compared to the commercial early season southern highbush blueberry cultivar 'Suziblue' and 'Camellia'. The new variety is early season and begins flowering and ripening later than 'Suziblue', but similar to the time of 'Camellia'. 'TH-896' has large berries with smaller scar, and lighter color than berries of 'Suziblue' and 'Camellia'. The berries of 'TH-896' are firmer and have flavor with a more balanced acidity to sweetness compared to 'Suziblue' and 'Camellia' at Alapaha (Table 1). When compared to 'Suziblue', fruit of 'TH-896' are larger, with lighter color, smaller scar, firmer berries, and flavor with balanced acidity to sweetness (Table 1). No notable diseases or other pest problems have been observed for the new variety that are not also common for other varieties. The new variety is estimated to have a chilling requirement of about 300-400 hours, or more, below about 45° F. (based on comparison of flowering dates with those of known standard cultivars) when produced under typical low to mid chill production regions. Additional comparison data of 'TH-896' with 'Suziblue' and 'Camellia' are presented in the table below.

TABLE 1

Plant and fruit ratings for 'TH-896' and standards grown in Alapaha, GA. Data represents a 3 Year average (2014, 2015, and 2016). Rating scales are based on a 1 to 10 score, with 1 being the least desirable and 10 being the most desirable. Plants were established in 2010.

| | 'Suziblue' | 'Camellia' | 'TH-896' |
|---|---|---|---|
| Berry size | 8.0 | 8.8 | 8.5 |
| Berry scar | 7.3 | 7.0 | 8.1 |
| Berry color | 7.0 | 8.2 | 8.0 |
| Berry firmness | 7.6 | 7.5 | 8.6 |
| Berry flavor | 7.2 | 8.0 | 8.3 |
| Cropping | 7.0 | 6.0 | 6.0 |
| Plant vigor | 7.5 | 9.5 | 7.0 |
| Date of 50% flowering | February 28 | March 10 | March 9 |
| Date of 50% ripening | May 7 | May 13 | May 12 |
| Fruit development period (days) | 68 | 64 | 64 |

BRIEF DESCRIPTION OF THE DRAWINGS

The accompanying colored photographic illustrations show the overall appearance and distinct characteristics of the new cultivar of *Vaccinium corymbosum* 'TH-896' showing the colors as true as possible. Colors in the photographs may differ slightly from the color values cited in the detailed botanical description, which accurately describes the colors of the new *Vaccinium corymbosum* 'TH-896'. Photographs were taken of plants grown outdoors in Alapaha, Ga. during different years.

The photograph labeled

Figure 1:
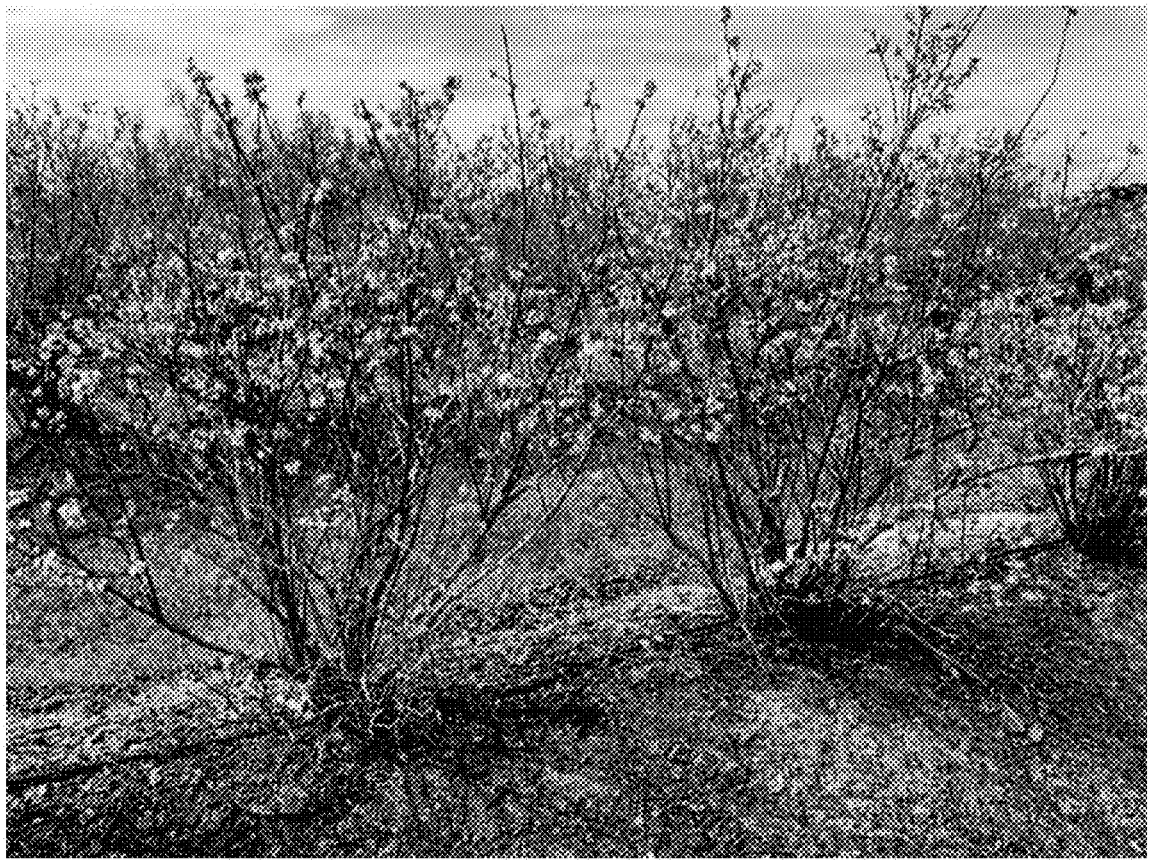
FIG. 1 depicts typical 6-year old plants of 'TH-896' during flowering. Photographs were taken in March 2019.
Figure 2:
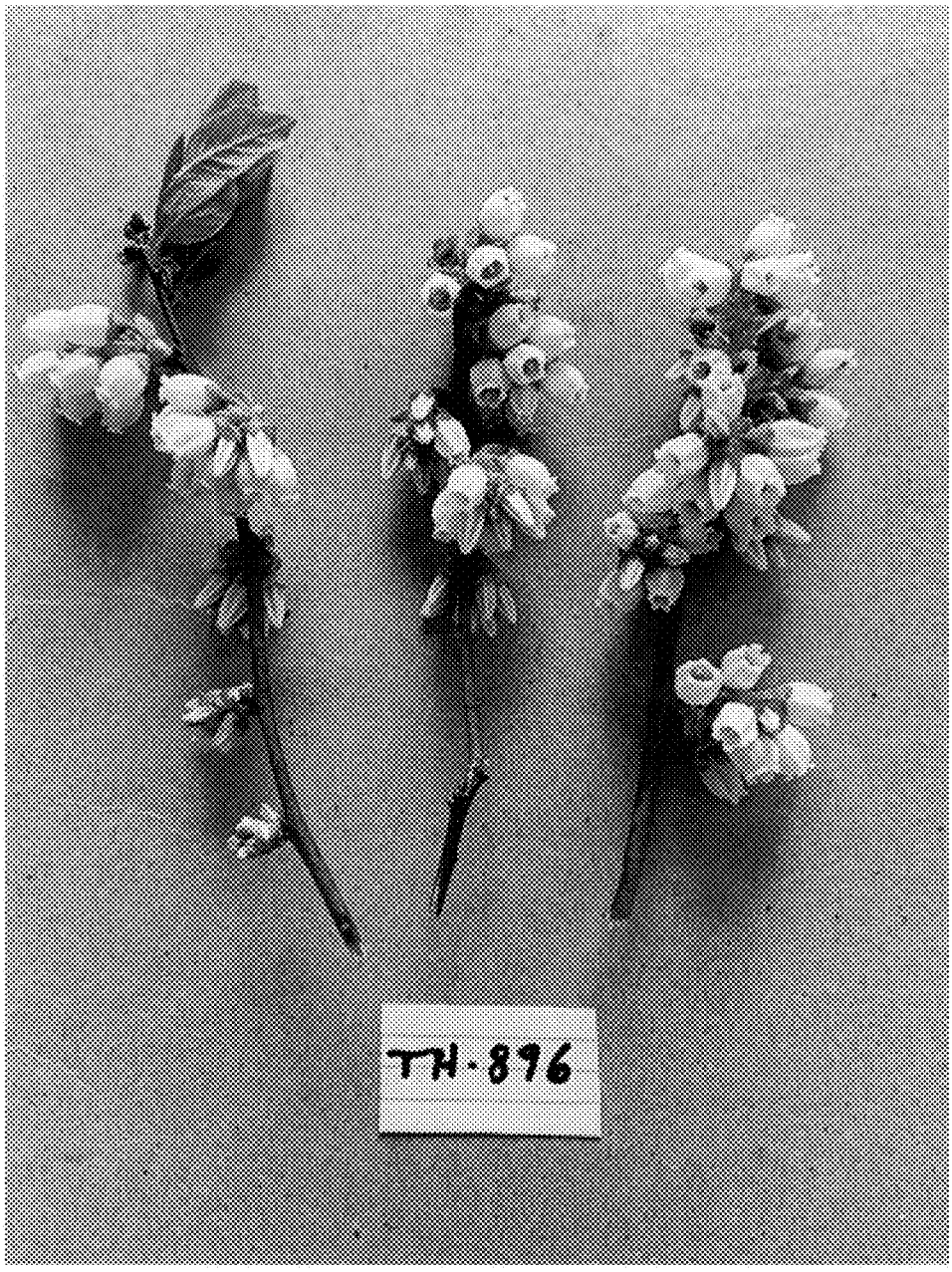

The photograph labeled FIG. 2 was taken in March 2021 and shows a close-up of flowering branches of 'TH-896'.

Figure 3:
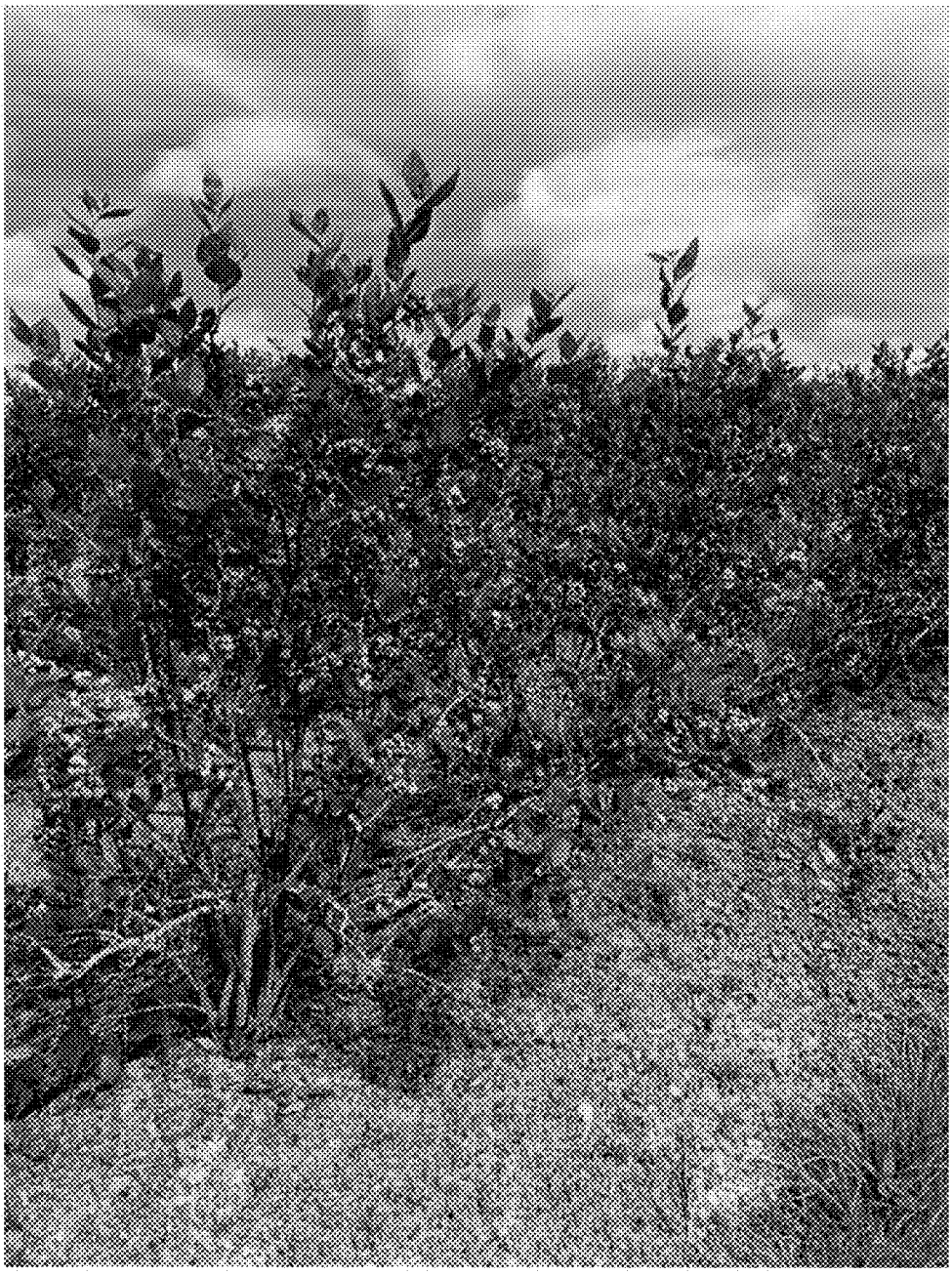

The photograph labeled FIG. 3 depicts 6-year old 'TH-896' plants during fruit ripening. Photographs were taken in May 2019.

Figure 4:
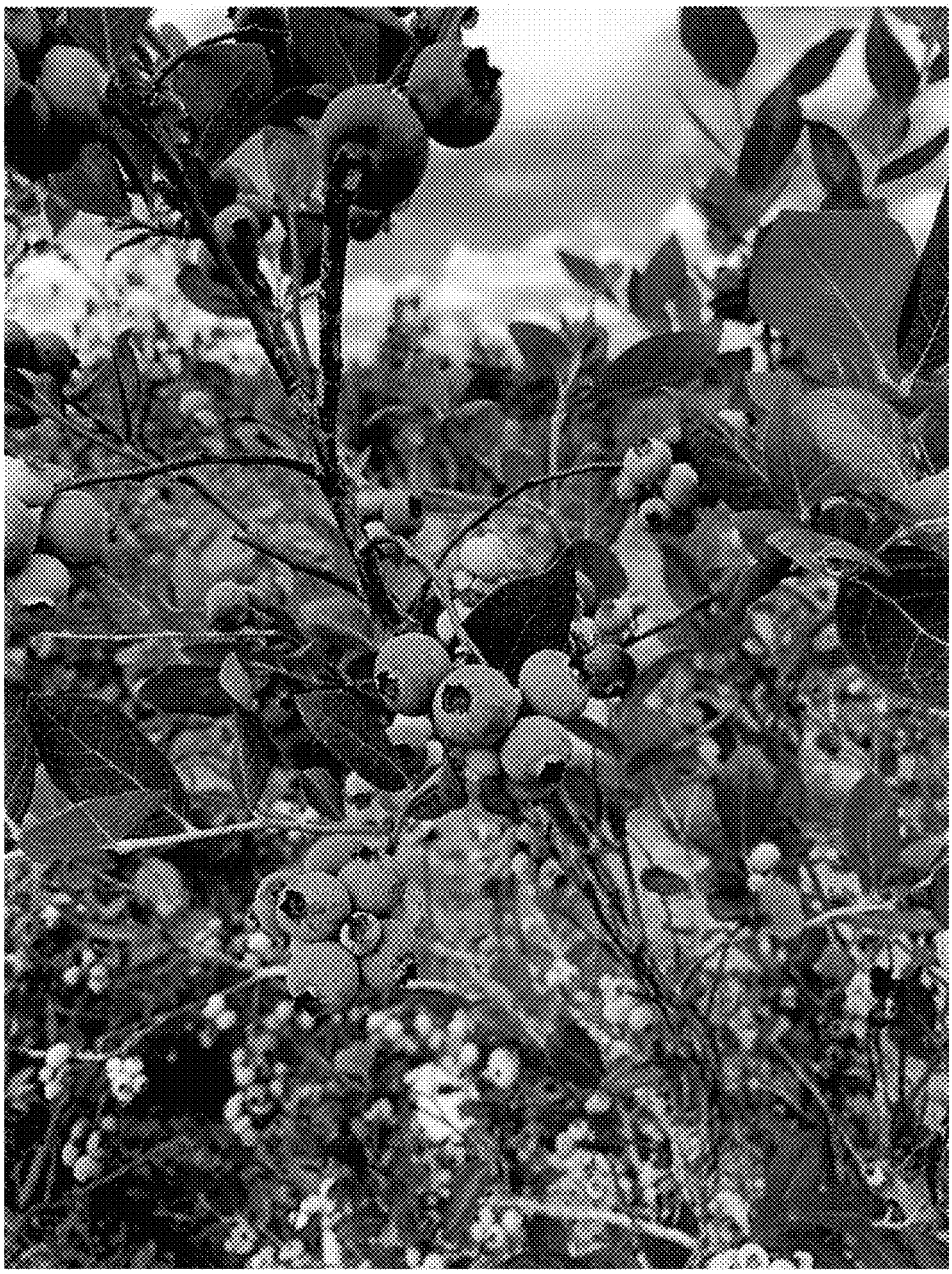

The photograph labeled FIG. 4 depicts a close-up view of 'TH-896' fruit as it matures showing good scar and color, taken in May 2019.

Figure 5A:
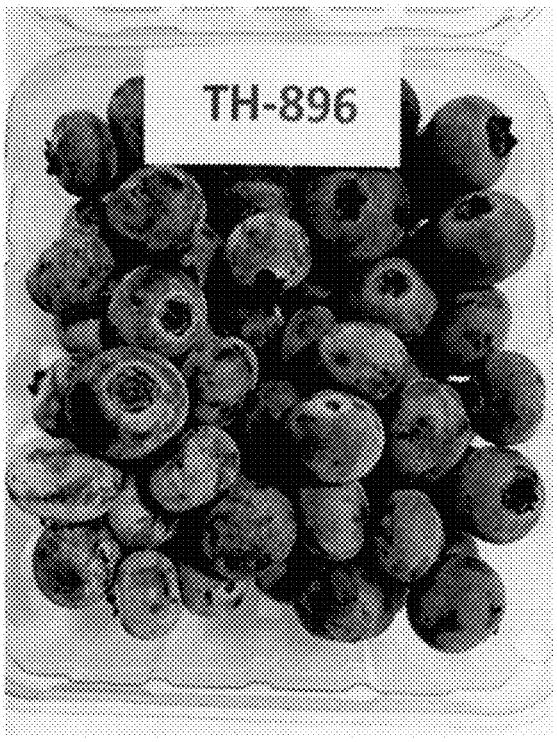
Figure 5B:
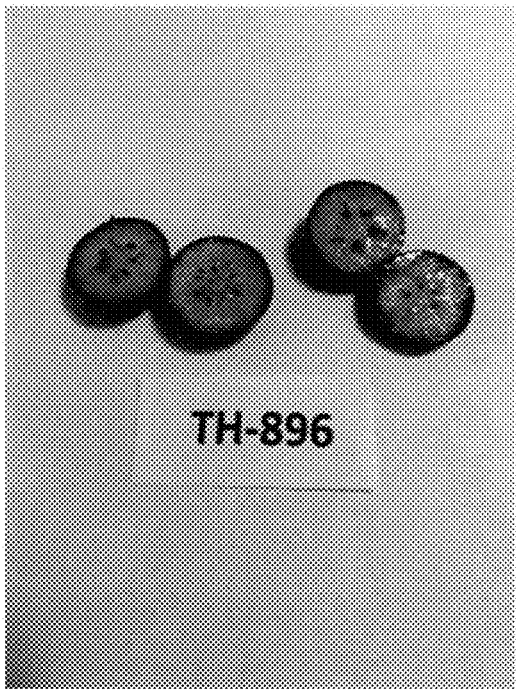

The photographs labeled FIGS. 5A-5B depict close-up views of 'TH-896' fruit. FIG. 5A is a close-up view of fruit of 'TH-896' in a container, and FIG. 5B shows a cross sectional view of the interior of the fruit taken in May 2021

Figure 6:
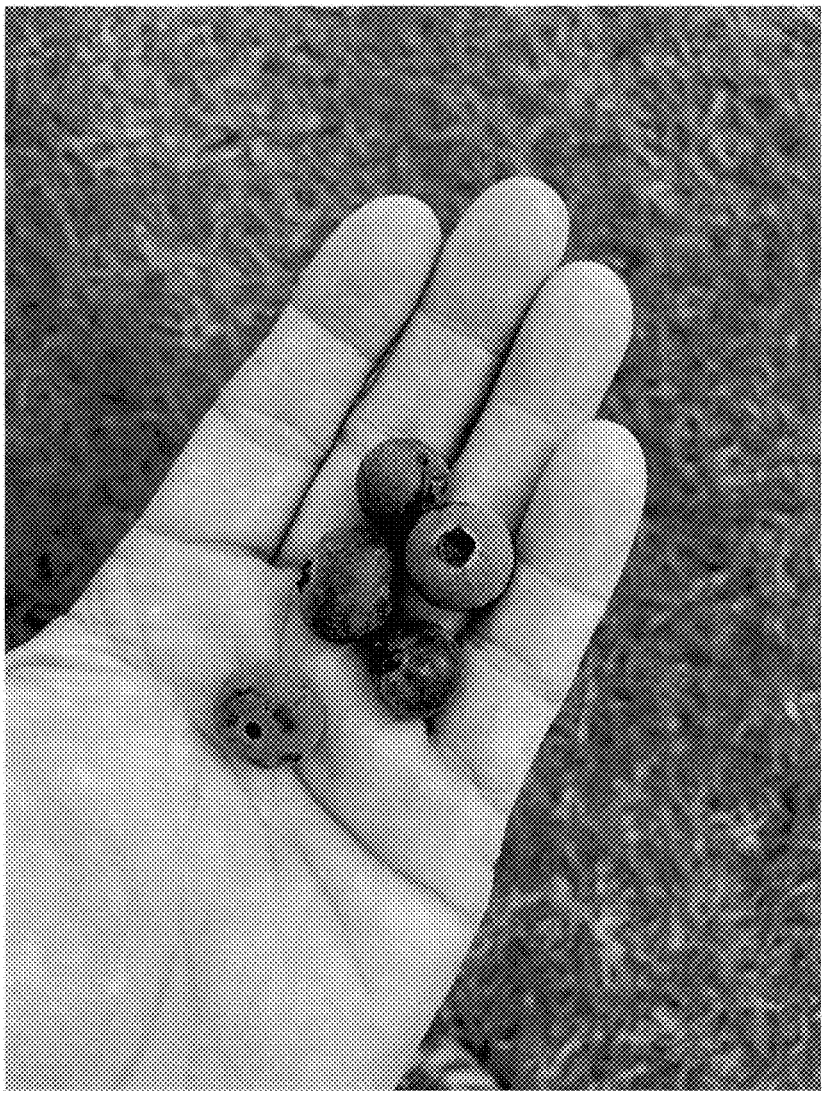

The photograph labeled FIG. 6 depicts a close-up view of ripe fruit of 'TH-896' in a human hand, illustrating the relative size of the fruit taken in May 2021

DETAILED BOTANICAL DESCRIPTION

The following traits have been consistently observed in the original plant of this new variety and in asexually propagated progeny grown in Alapaha and Griffin, Ga., and, to the best knowledge of the inventor, their combination forms the unique characteristics of the new variety *Vaccinium corymbosum* 'TH-896'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Vaccinium corymbosum* cultivar named 'TH-896'. Where dimensions, sizes, colors, and other characteristics are given, it is to be understood that such characteristics are approximations and averages set forth as accurately as practicable. Data were collected between the years of 2017-2021 from horticulture farms and nurseries in Alapaha, Ga. from 4 to 6-year-old plants (planted in the field with supplemental irrigation). In this region, the long-term average annual low temperature ranges from about 54° F. to 58° F., and the average annual high temperature for the year ranges from about 78° F. to 82° F.

Botanical classification: *Vaccinium corymbosum* 'TH-896'.

*Commercial classification.*—Fruit-bearing shrub.

*Parentage.*—Cross of *Vaccinium corymbosum* 'TH-622' (non-patented breeding selection, female parent) and 'Bluecrisp' (U.S. Plant Pat. No. 11,033, male parent)

Growth and propagation:

*Propagation type.*—Vegetative by softwood cuttings.

*Growth rate.*—Plant vigor is medium, canopy tends to stay compact.

*Root description.*—Fibrous.

Plant description:

*Growth habit.*—Plant is semi-upright, with dominant vertical growth. Compact, dense canopy with some tendency to spreading. Two to 4 main canes arising from the original crown, and multiple branching of shoots from those canes typically less than about 10 cm above ground.

*Usage.*—Primarily to be used as fresh fruit for shipping and processing markets.

*Productivity.*—Medium to high yielding. Yields of about 5 to 8 lbs per plant each year on plants 4 years old or older grown under well fertilized and irrigated field conditions. Frost protection may be useful to reach yield potential in some years.

*Size of plant.*—Plant is about 1.2 to 1.5 m tall by about 4 years. The plant crown, or base, is very narrow, typically about 10 to 15 cm in diameter. Upper portion of plant canopy reaches about 1.2 to 1.4 m in diameter by about 4 years.

*Cold hardiness.*—Similar to other early to mid-ripening southern highbush varieties such as 'Suziblue' (U.S. Plant Pat. No. 21,167) and 'Camellia' (U.S. Plant Pat. No. 18,151).

*Disease resistance.*—No notable disease resistance or susceptibility observed. Typical for early season southern highbush such as 'Suziblue' and 'Camellia'.

*Chilling requirement.*—Plants are medium chill, requiring about 300 to 400 hours, or more, of temperatures at or below 45° F. (7° C.) to induce normal leafing and flowering during the spring under conventional dormant production systems. The chill requirement is less than the female parent 'TH-622' (non-patented breeding selection; 500 to 600 hours of chilling required) and more similar to the male parent 'Bluecrisp' (U.S. Plant Pat. No. 11,033, 350 to 400 hours of chilling required).

*Leafing*.—Plants tend to break sufficient leaf buds simultaneously with, or shortly after, anthesis.

*Canes*.—Main cane base diameter about 20 to 30 mm, color most near Brown N200C to Grey 201C; two year old cane diameter 10 to 15 mm, color transitioning from Yellow Green 145B to Greyed Orange 166C to Grey 201C; current season wood diameter about 5 to 10 mm, color Yellow Green 145B; one year old shoots have the same color as current season shoots, Yellow Green 145B.

*Fruiting wood*.—Moderate number of twigs (5 to 8 common) of about 15 to 25 cm in length, with internode lengths of about 20 to 25 mm common; plants flower and fruit on one-year-old shoots.

Foliage:

*Leaf color healthy mature leaves*.—Top side of leaf color is Green 137B to Green N137C, under side of leaf color is Green 138B.

*Leaf arrangement*.—Alternate, simple.

*Leaf shape*.—Nearly elliptic.

*Leaf margins*.—Some undulation observed in younger leaves, becoming nearly entire by maturity.

*Leaf venation*.—Pinnate with slight netting.

*Leaf apices*.—Broadly acute.

*Leaf bases*.—Broadly acute.

*Leaf dimensions*.—Length: about 70 to 90 mm; width: about 35 to 45 mm.

*Petioles*.—Small, about 5.0 to 7.0 mm long, about 2.0 to 3.0 mm wide; Color: Yellow Green 145C.

*Texture*.—Both upper and lower leaf surfaces, glaucous.

Flowers:

*Date of* 50% *anthesis*.—3-year average March 9 in southeast Georgia.

*Flower shape*.—Urceolate; average inflorescence length is about 14.0 to 16.0 mm.

*Flower bud*.—Number: high, averaging about 4 to 6 buds per fruiting shoot; anthocyanin coloration is weak.

*Flowers per cluster*.—About 7 to 10 common.

*Flower fragrance*.—None observed.

*Corolla color*.—White NN 155C to NN 155D.

*Corolla length*.—About 9.0 to 10.0 mm.

*Corolla width*.—About 8.0 to 9.0 mm.

*Corolla aperture width*.—About 3.5 to 4.5 mm.

*Flower peduncle*.—Length about 14.0 to 16.0 mm; Color: Green 138D.

*Flower pedicel*.—Length about 4.0 to 5.0 mm; Color: Green 138D.

*Calyx* (*with sepals*).—Diameter: about 7.0 to 8.0 mm; Color: sepals Green 138C; calyx center Green 1386.

*Stamen*.—Length: about 6.0 to 7.0 mm; number per flower: about 10; filament color: Green White 157A.

*Style*.—Length: about 9.0 to 10.0 mm; Color: Yellow Green 145B to 145C.

*Pistil*.—Length: about 12.0 to 13.0 mm; ovary color: Green 138C.

*Anther*.—Length: about 4.0 to 5.0 mm; number: 10; Color: Greyed Orange 165B.

*Pollen*.—Abundance: high; Color: Yellow White 158C.

*Compatibility*.—The cultivar has a moderate degree of self-compatibility.

Fruit:

*Date of* 50% *maturity*.—3-year average around May 12 in southeast Georgia.

*Fruit development period*.—About 64 days in southeast Georgia.

*Berry color*.—With wax Violet Blue 98D; with wax removed Black 203A.

*Berry flesh color*.—Green White 157C.

*Berry surface wax abundance*.—Medium.

*Berry weight*.—$1^{st}$ harvest: about 3.3 to 3.7 g; $2^{nd}$ harvest: about 2.4 to 2.9 g.

*Berry size*.—Height from calyx to scar: about 10 to 13 mm; diameter: about 15 to 19 mm.

*Berry shape*.—Somewhat disk shaped.

*Fruit stem scar*.—Small to medium, dry, with no tearing upon harvest.

*Fruit calyx*.—Depth medium, about 1.0 to 3.0 mm; width medium, about 5.0 to 7.0 mm; sepals not very prominent, turned inwards or semi-erect when present, less than about 1.0 mm.

*Berry firmness*.—Very firm.

*Berry flavor and texture*.—Well-balanced acidity to sweetness; crisp texture.

*Storage quality*.—Very good (12-14 days).

*Suitability for mechanical harvesting*.—Not likely suitable.

*Uses*.—Primarily intended for fresh fruit for shipping and processing markets.

Seed:

*Seed abundance in fruit*.—Medium, with about 5 to 10 fully developed seeds/berry.

*Seed color*.—Greyed Orange 166B.

*Seed dry weight*.—About 56.4 mg per 100 seed.

*Seed size*.—About 1.7 to 2.2 mm long.

It is claimed:

1. A new and distinct cultivar of the *Vaccinium* plant named 'TH-896' as illustrated and described herein.

* * * * *